United States Patent [19]

Dulebohn

[11] Patent Number: 5,065,516

[45] Date of Patent: Nov. 19, 1991

[54] DISASSEMBLABLE SCISSORS MEANS

[75] Inventor: David H. Dulebohn, Tonka Bay, Minn.

[73] Assignee: Andrew Tool Company, Plymouth, Minn.

[21] Appl. No.: 433,019

[22] Filed: Nov. 6, 1989

Related U.S. Application Data

[63] Continuation-in-part of Ser. No. 49,109, May 11, 1987, abandoned.

[51] Int. Cl.⁵ ............................................. B26B 13/00
[52] U.S. Cl. ....................................... 30/245; 30/258; 30/260; 606/208
[58] Field of Search .................. 30/254, 258, 260, 261, 30/245, 236, 234, 269; 606/174, 205, 208

[56] References Cited

U.S. PATENT DOCUMENTS

| | | | |
|---|---|---|---|
| 434,345 | 8/1890 | Koelsch | 30/269 |
| 973,296 | 10/1910 | Peddle | 606/174 |
| 2,619,965 | 12/1952 | Goldstone . | |
| 2,652,832 | 9/1953 | Castroveijo . | |
| 2,696,045 | 12/1954 | Blodgett | 30/269 |
| 2,742,698 | 4/1956 | McGary et al. | 30/254 |
| 3,550,595 | 12/1970 | Laufe | 128/323 |
| 3,562,908 | 2/1971 | Rogers | 606/208 |
| 3,893,199 | 7/1975 | Todaro | 30/258 |
| 4,452,246 | 6/1984 | Bader et al. | 128/340 |
| 4,478,221 | 10/1984 | Heiss | 128/334 R |
| 4,823,792 | 4/1989 | Dulebohn et al. | 606/208 |
| 4,890,388 | 1/1990 | Rose | 30/260 |
| 4,949,717 | 8/1990 | Shaw | 606/174 |

*Primary Examiner*—Mark Rosenbaum
*Assistant Examiner*—Hwei-Siu Payer
*Attorney, Agent, or Firm*—Zarley, McKee, Thomte, Voorhees & Sease

[57] ABSTRACT disassemblable scissors which utilizes a releasable pivot joint between pivotable scissor halves. The pivot joint is formed in the scissor halves between the blades and the handles of the scissor. The scissors halves are pivotally retained together over a range of cutting motions by a retaining assembly. The retaining assembly retains a portion of one of the scissors halves movably within a retaining portion of the other of said scissors halves at least over the range of cutting motions. To release and disassemble the scissors, the scissors halves must be pivoted at least past the range of cutting motions to a point where the portion of the one scissor half is no longer retained by the retaining portion of the other scissors half. In this position, the two halves can be transversely pulled apart.

5 Claims, 5 Drawing Sheets

DISASSEMBLABLE SCISSORS MEANS

RELATED APPLICATION

This is a continuation-in-part application to co-owned, co-pending U.S. Ser. No. 49,109 filed May 11, 1987 by inventor David H. Dulebohn, now abandoned.

BACKGROUND OF THE INVENTION

1. Field of the Invention

This invention relates to a scissors means, and in particular, an easily disassemblable and assemblable scissors means facilitating quick and easy separation and cleaning of the scissors halves, and easy assembly for reuse. An alternative embodiment presents a disassemblable scissors which is also more economical to manufacture.

2. Problems in the Art

Conventional scissors generally are secured together by rivets, screws, and other similar fasteners. Such rivets, screws, and the like not only serve to fasten together the scissors halves, but also function as the pivot point. Additionally, they must serve to reliably keep the scissor halves in closely adjacent position to insure optimal cutting efficiency of the scissor blades.

A primary problem with scissors is that, since the blades come together and overlap to create the cutting action, debris and other material accumulates in-between the blades and in the pivot of the scissor halves. Such accumulation can reduce the efficiency of the scissors, and even affect their operability. In medical uses, there is also a problem with contamination.

Scissors which have permanent securing means, such as rivets, simply do not allow the scissor halves to be disassembled, separated, and cleaned. Portions of the scissor blades adjacent to the pivot are simply not reachable for cleaning, nor is the pivot between the blades. Even with stringent cleaning techniques, build-up of debris or material in the pivot can eventually impair pivoting of the scissor halves.

Though technically, these types of scissors are disassemblable, it requires use of tools and is generally neither quick nor easy. Debris and foreign material problems exist.

Some other types of conventional scissors, though the halves are not permanently secured, are secured in a manner not easily disassemblable. Because of the need for a strong and stable pivot, and close tolerance between the cutting blades to insure accurate and efficient cutting, many times a screw or bolt and nut arrangement is used so that the blades can be continually tightened together.

These problems are particularly acute in smaller scissors, for example, with regard to those used in medical microsurgery. Build-up of debris causing corrosion can even cause removable securing means such as screws or bolts to become locked or bound, which prevents them from being removable.

No satisfactory solution is known for a scissors which combines a stable, strong, and efficient pivot mechanism, while at the same time providing for quick and easy separation of scissor halves without the need for tools. The problem is significant, especially in fields of use such as medical applications.

It is known that in some larger shearing or cutting devices, such as garden shears or the like, the halves of the instrument are disassemblable. However, this is accomplished by requiring a slot in one half, and a permanently attached stem and stem head on the other half. The head is elongated along one axis, and the slot is positioned on the one scissor half so that when the halves are rotated almost perpendicular to one another, the stem head is removable from the slot, allowing the scissor halves to be separated. When the halves are assembled, the stem head cannot be removed from the slot during the normal cutting range of the scissors. Somewhat of a similar configuration is shown in U.S. Pat. No. 2,619,965 for larger type scissors used in surgery. This solution is not satisfactory. Because of the necessary tolerances, the two scissor halves necessarily will have significant play between them. Therefore, this type of arrangement does not allow the scissors to be manufactured to optimum accuracy. Also, the stem head represents a projection from the side of the scissors which is many times disadvantageous.

Other medical instruments such as those seen in U.S. Pat. No. 3,550,595 have separability of two halves of the instrument as a feature, but the instrument halves are joined at their rear ends and the pivot consists only of a slot insertable over a pin in the other half. Thus, similar problems of play between halves of the instrument, and the problem of the two halves being separated unintentionally during use exist.

There is therefore a real need for a solution to the problems discussed above. It is therefore a primary object of the present invention to provide a scissor means which improves over and solves the problems and deficiencies in the art.

Another object of the invention is to provide a scissors means which is easily disassemblable and assemblable.

A further object of the present invention is to provide a scissors means which is stable, accurate, and efficient.

Another object of the present invention is to provide a scissors means which is easily disassembled and assembled without having to orientate scissors halves to extreme positions, or to require tools or other items to separate halves.

A further object of the present invention is to provide a scissors means which is easily and completely cleanable and serviceable.

Another object of the present invention is to provide a scissor means which is economical to manufacture, has a minimum of parts and is durable.

These and other objects, features and advantages of the present invention will become apparent with reference to the accompanying specification and drawings.

SUMMARY OF THE INVENTION

The present invention utilizes a pair of scissor halves which are pivotally but releasably connected. A releasable pivot means is formed in the scissor halves between the scissor blades and the handles of the scissor halves.

The scissors have blades which operate with stability, as well as accurately and efficiently. The pivot means is associated with a pair of scissor halves and defines the pivot point between the scissors halves. The pivot means creates the stable, accurate, and efficient pivot point but does not require separable hardware such as bolts and nuts, threaded screws and apertures, or other securing means, or require any tools to assemble or disassemble the halves from one another.

The pivot means both allows pivoting of the scissor halves and retains the scissor halves in cutting position over the range of cutting movements of the scissors blades. When assembled, the scissor halves are retained in that position until pivoted with respect to one another past a position outside the cutting range of the scissors. The halves can then be quickly and easily separated or disassembled.

The pivot means therefore functions as if the scissors halves were bound together so that there is no play, looseness, or potential for the same over the range of cutting motions. A retaining means is associated with the pivot means to accomplish this function which achieves the advantages of scissors which are bound together, yet allows them to be quickly and easily disassemblable for cleaning or repair.

In one embodiment of the present invention the pivot means comprises a pin which is unitary with the first scissor half behind the blade for that half and which extends transversely or generally perpendicularly to the plane in which that blade moves during pivoting. Correspondingly, an aperture exists in the other scissor half perpendicular to the plane of the pivotable movement of its blade. The pin and aperture therefore comprise the pivot point or axis for the scissors. The pin is slidably and pivotally insertable into the aperture.

A flange or cam means is also formed in the first scissor half. It extends generally in the same plane as the movement of its blade, or in a closely parallel plane. Correspondingly, a slot is formed in the other scissor half which mateably and slidingly receives the cam or flange. The pin and aperture therefore form the rotational pivot for the scissor halves, while the flange in the slot retains the scissor halves together during their pivotable movement in cutting procedures.

The scissor halves are separable because the flange and slot are configured so that when the blades are moved past a conventional maximum opened cutting position, the flange moves out of the slot. Thus, the halves can be separated by pulling transversely to their longitudinal axes. Likewise, the halves are easily assemblable by performing a reverse procedure.

It can therefore be seen that by altering the length or configuration of the flange or the slot, various maximum opening positions for the blades can be created. It does not, however, require that the halves be rotated to be approximately perpendicular from one another to separate the halves.

Such a pivot means comprises a minimum number of parts, does not require tools to separate the halves, and provides easily cleanable parts and surfaces. The pivot means can be used with most types of scissors and is useful with many different shapes and types of scissor blades.

An additional optional feature includes the use of a releasable means at the rear end of the handle of the scissors. In order to bias the scissor blades open from a closed position, it is conventional to bend or shape the rearwardmost outer ends of the handle of each scissor half towards one another and then secure them to one another. This provides a spring effect to bias the blades open. Conventionally, a rectangular hole was formed in one scissor half and then a T-shaped end in the other was twisted and then inserted into the rectangular hole to secure the two halves. This allowed for the ends to be releasable. However, it required that one end or the other, or both, be twisted to allow the one end to be withdrawn from the rectangular opening. This was not only somewhat difficult to do, it also created a twisting in the handles which might affect instrument shape and performance.

Therefore, an optional alternative feature of the present invention is to have a releasable securing of the rearward ends of the handles whereby one handle of one scissor half has a slot extending from its very end inwardly along its longitudinal axis. The outer rear end of the other scissor half has a T-shaped head whereby the sole leg extending down from the T-shaped head would be slidably inserted into the slot on the other scissor half. No twisting or bending of the handle is necessary, yet the ends ar secured together and create the biasing force on the blades. Also, no hole needs to be produced in either handle, which is more difficult and costly than a slot and a T-shaped head. Also, such configurations (slot and T-shaped head) are easily producable by traveling wire electrical discharge machine (EDM) processes.

Another embodiment of the present invention is similar to the first described embodiment, except it has unique and beneficial features which provide it with advantages not present in the first described embodiment. The second embodiment also can utilize a pin which is connected to, but not unitary with, one scissor half and which extends transversely and is mateable into a pivot aperture in the other scissor half. The pivot aperture can either be partially or fully extended through the other scissor half, and can be a circular bore or simply a partial-circular having a portion of its perimeter open.

Unlike the first described embodiment, the second embodiment does not include a flange or cam means which is separately formed and extends from one of the scissor halves to fit within a narrow slot in the other scissor half and does not include a unitary pivot pin.

The first described embodiment with the flange or cam member allows disassembly and assembly of the scissors halves by virtue of the length or configuration of the cam member. Production of the cam member, however, requires intricate and supplemental machining which is costly and time consuming, as does production of the unitary pivot pin. The cam member also presents narrow surfaces and junction points which are susceptible to catching or holding debris, which is undesired and counterproductive to the goals of the present invention.

The precision required of the scissors, and the materials of which they are made of, allows scissors, made according to the invention, to be produced by each scissors half being cut with an electrical discharge machine (EDM), and in particular, a traveling wire EDM machine. This process is advantageous for these types of instruments because it can make intricate and extremely accurate cuts from even hard metals which reduces or can even eliminate the requirement for additional steps such as supplemental machining of different features. A discussion of the EDM process can be found at co-owned U.S. Pat. No. 4,761,028, by inventor Dulebohn, issued Aug. 2, 1988, which is incorporated by reference herein.

DETAILED DESCRIPTION OF THE PREFERRED EMBODIMENT

Figures 1, 2:
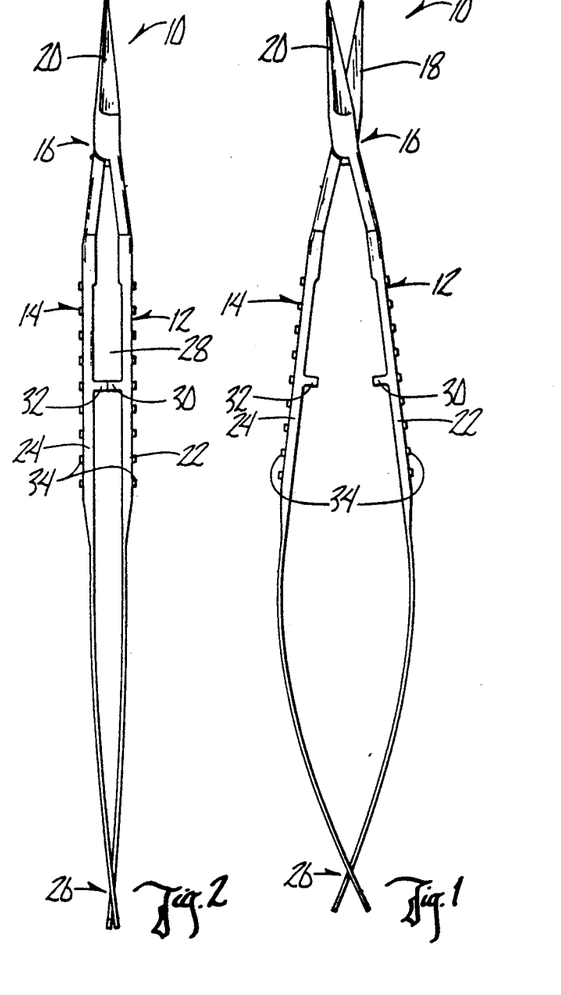
FIG. 1 is a top plan view of the one embodiment of the invention with the scissor blades biased to an open position.
FIG. 2 is a top a top plan view of the embodiment of FIG. 1 showing the handle members pushed together which in turn shows the blades in a closed position.
Figure 3:
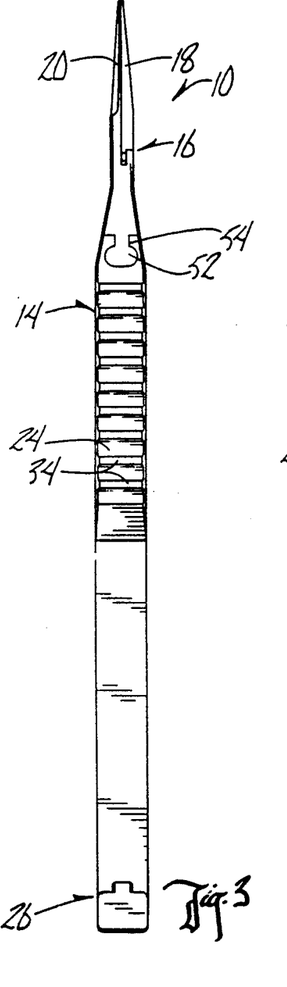
FIG. 3 is a side view of the embodiment of FIG. 1.

With reference to the drawings, and particularly FIGS. 1-3, there is shown a first preferred embodiment of a scissors means 10 according to the present invention. Scissors half 12 is pivotally connected to scissor half 14 by a pivot means which is generally indicated by reference numeral 16. Scissor halves 12 and 14 have blades 18 and 20 forward of pivot means 16, and handles 22 and 24 rearward of pivot means 16.

Each scissor half 12 and 14 has a general longitudinal axis along its elongated length. To enable cutting action, blades 18 and 20 must overlap. Therefore, blades 18 and 20 pivotally move in generally closely adjacent parallel planes which somewhat generally conform with the planes of movement of their respective longitudinal axes.

FIG. 1 shows the scissors halves 12, 14 in their normal state if no forces are exerted on handles 22 and 24. The rearward ends of handles 22 and 24 include a releasable connection generally indicated by reference numeral 26. This optional feature can serve two purposes. First, connecting the rear ends of the handles prevents separation of the disassemblable scissor halves 12 and 14 during use. Secondly, by pre-bending or shaping the rear portions of handles 22 and 24 so that they bend towards one another, provides the necessary spring or biasing force to bias blades 18 and 20 open when handles 22 and 24 are connected at releasable connection 26 and halves 12 and 14 are connected at pivot means 16.

It is also pointed out that handles 22 and 24 are angled away from each other for a short distance behind pivot means 16. This allows a gap, generally indicated by reference numeral 28. Additionally, stop members 30 and 32 can be correspondingly positioned on the inside of handles 22 and 24 so that when the handles are brought together, stop members 30 and 32 abut and stop any continued movement so that blades 18 and 20 can be aligned upon closure. The outside portions of handles 22 and 24 can contain protrusions 34 or similar elements to assist the user to grip handles 22 and 24.

FIG. 3 depicts that the handles 22 and 24 can be of a wide and flat configuration to also assist in gripping. It is pointed out that the pivot means 16 of the present invention is internally contained so that there are no protrusions from or around the blades 18 and 20, which might catch or otherwise disturb cutting or surrounding material.

Figure 7:
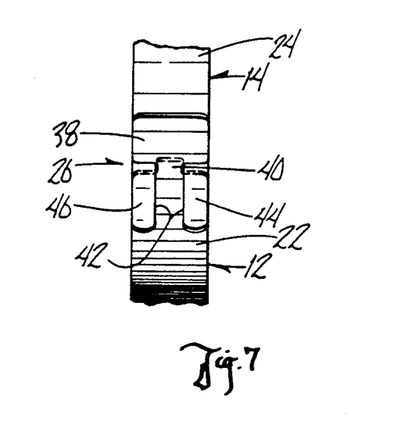
FIG. 7 is a fragmented view of the end releasable connection for the rearward ends of handles of the embodiment of FIG. 1.

FIGS. 3 and 7 show that releasable connection 26 is comprised of handle member 22 having a T-shaped rearward end which includes a head 38 and a narrow leg 40. Handle member 24 simply includes a slot 42 (see FIG. 7), bounded by legs 44 and 46 (see FIG. 7). The T-shaped rearward end can be released from slot 42 simply by sliding it out of the end of slot 42. No twisting of handles 22 and 24 is required.

Figure 4:
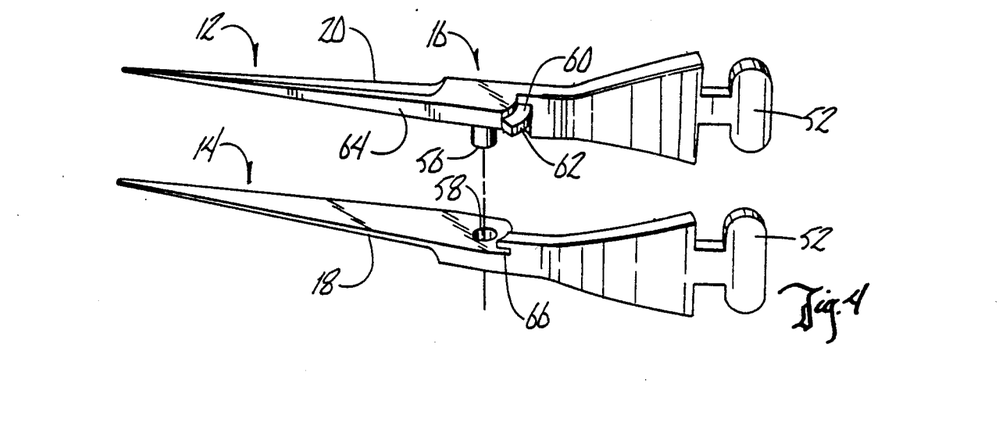
FIG. 4 is an exploded perspective view of the blades, pivot mechanism, and an optional removable tip means of the embodiment shown in FIG. 1.

FIGS. 3 and 4 depict that the forward portion of scissor means 10 is removable from the remaining part of handles 22, 24. The front portions of halves 12 and 14 of scissor means 10 (see FIG. 4) consist of blades 18 and 20, pivot means 16, and a portion of handles 22 and 24 directly adjacent pivot means 16. The rear portion of scissor means 10 consists of the remainder of handles 22 and 24. The front portions of scissors halves 12 and 14 ca be generally referred to as removable tips. The front portions of each scissor half 12 and 14 have a T-member 52 which fits within a slot 54. In the preferred embodiment, T-member 52 fits slot 54 by interference, that is, T-member 52 is slightly larger than slot 54 before it is inserted. Insertion therefore causes the legs around slot 54 to somewhat slightly and resiliently spread and T-member 52 is therefore frictionally secured within slot 54.

Figure 5:
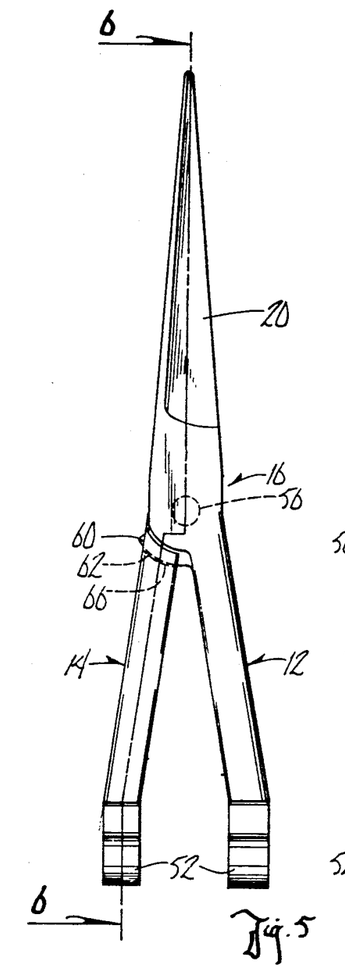
FIG. 5 is a top plan view of the scissor parts of FIG. 4 shown in assembled form with the blades closed.
Figure 6:
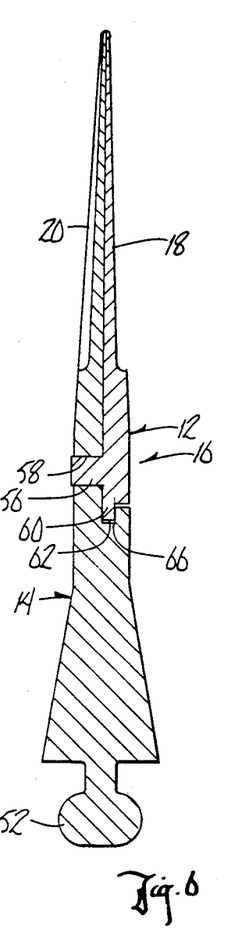
FIG. 6 is a sectional view taken along lines 6—6 of FIG. 5.

FIGS. 4–6 more specifically depict the configuration of a preferred embodiment for pivot means 16. A pin 56 is unitary with and extends from the inner-facing surface of scissor half 12 at the location of pivot means 16. Pin 56 extends generally perpendicularly to the plane defined by the pivotal movement of blade 20 during cutting action. Correspondingly, an aperture 58 extends into the inner surface of scissor half 14 to slidably and pivotally receive pin 56 at the location of pivot means 16 of scissor means 10. The axis of aperture 58 is generally perpendicular to the plane of movement of blade 18.

Scissors half 12 also includes a flange or cam 60. In the preferred embodiment of FIG. 4, flange 60 extends somewhat rearwardly and somewhat outwardly from behind blade 20 and pin 56. Flange 60 has a curved rearward edge 62 which extends a little beyond the plane of edge 64 of blade 20.

Scissor half 14 includes a corresponding slot 66 which is rearward of aperture 58. Slot 66 is configured so as to receive flange 60 only when pin 56 is inserted into aperture 58. Slot 66 retains flange 60 and disallows separation of scissor halves 12 and 14 during angular orientation of the two halves over a range from a closed position, where blades 18 and 20 are closed, to a maximum opened position, where the blades 18 and 20 are opened.

It is to be understood that flange 60 and slot 66 are configured so that when scissor half 12 is angularly pivoted a sufficient distance (past the maximum opened position) from alignment with scissor half 14 (the closed position), that flange 60 is completely removed from slot 66; and at that point, scissor half 12 can be separated or disassembled from scissor half 14 by pulling halves 12 and 14 transversely apart which would pull pin 56 out of aperture 58.

It is to be understood that in the preferred embodiment, flange 60 and slot 66 cooperate so that scissor blades 18 and 20 can be opened and closed for a normal range of cutting purposes. That is, by altering the length and size of flange 60 and/or slot 66, the maximum opened position can be changed. Releasable connection 26 also is configured so that it is difficult, if not impossible, to separate flange 60 from slot 66 when rearward ends of handles 22 and 24 are connected.

FIG. 5 shows the shape and extension of curved edge 62 of flange 60. Also, FIG. 6 shows the close tolerances between pin 56 and aperture 58, and flange 60 and slot 66 in the preferred embodiment. In the position shown in FIG. 6, flange 60 and slot 66 prevent any transverse movement between scissor halves 12 and 14, whereas pin 56 and aperture 58 provide tight pivot surfaces and prevent any front to back motion between scissor halves 12 and 14. Therefore, a secure and reliable pivot joint is created which at the same time is easily disassemblable and assemblable.

Figure 8:
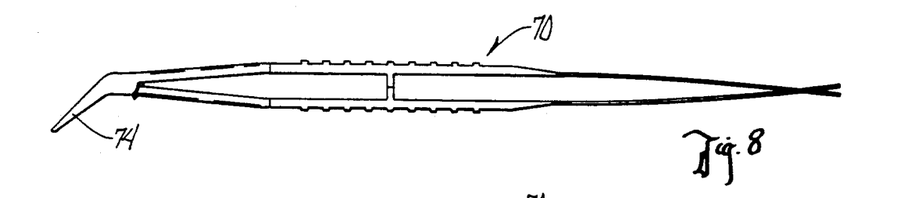
FIG. 8 is a top plan view of an alternative embodiment of scissors according to the present invention.
Figure 9:
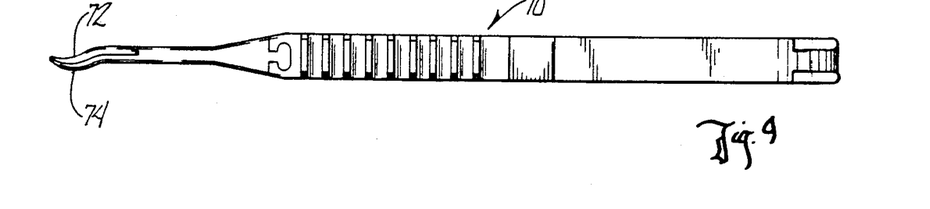
FIG. 9 is a side elevational view of the embodiment of FIG. 8.

FIGS. 8 and 9 depict alternative embodiments of scissors means 70. The difference from scissors means 10 is that blades 72 and 74 are both angled with regard to the longitudinal axis of scissor means 70 (FIG. 8), and curved with regard to that same axis (FIG. 9). It is therefore understood that the pivot means of the embodiment of FIG. 1 can be used with many types of scissors, as can be the releasable connection 26. It is to be understood that the included preferred embodiments are given by way of example only, and not by way of limitation to the invention, which is solely described by the claims herein. Variations obvious to one skilled in the art will be included within the invention defined by the claims.

FIGS. 10-21 depict other preferred embodiments of the present invention. As previously discussed, the embodiment shown in FIGS. 1-9 requires flange 60 with corresponding slot 66 in the scissors halves 12 and 14. Additionally, the embodiment of FIGS. 1-9 utilizes flange 60 to retain scissors halves together during pivotable movement, and flange 60 is configured to determine how far the two halves 12 and 14 are pivoted before they can be separated.

Flange 60 is a separately formed element which requires costly and time consuming machining to produce it from the one piece construction of scissor half 12. The same is true for the unitary pivot pin 56 of the embodiment of FIGS. 1-9, which is formed integrally with scissor half 12, and also requires costly and time-consuming secondary or additional machining after cutting the arms out in a first pass of the wire EDM machine.

The embodiment of FIGS. 10-21 has the advantage of not requiring an integral pivot pin 56, flange 60 or a correspondingly shaped slot 66, and thereby eliminates the need for substantial secondary machining. It is noted that flange 60 and pin 56 of the embodiment of FIGS. 1-9 are in close proximity, but are somewhat perpendicular in orientation, making the required secondary machining significantly costly. While the basic operation is similar between embodiments, the structure of the embodiment in FIGS. 10-21 has distinct and unique features and advantages as will be discussed in more detail below.

Figures 10, 11, 12, 13, 14:
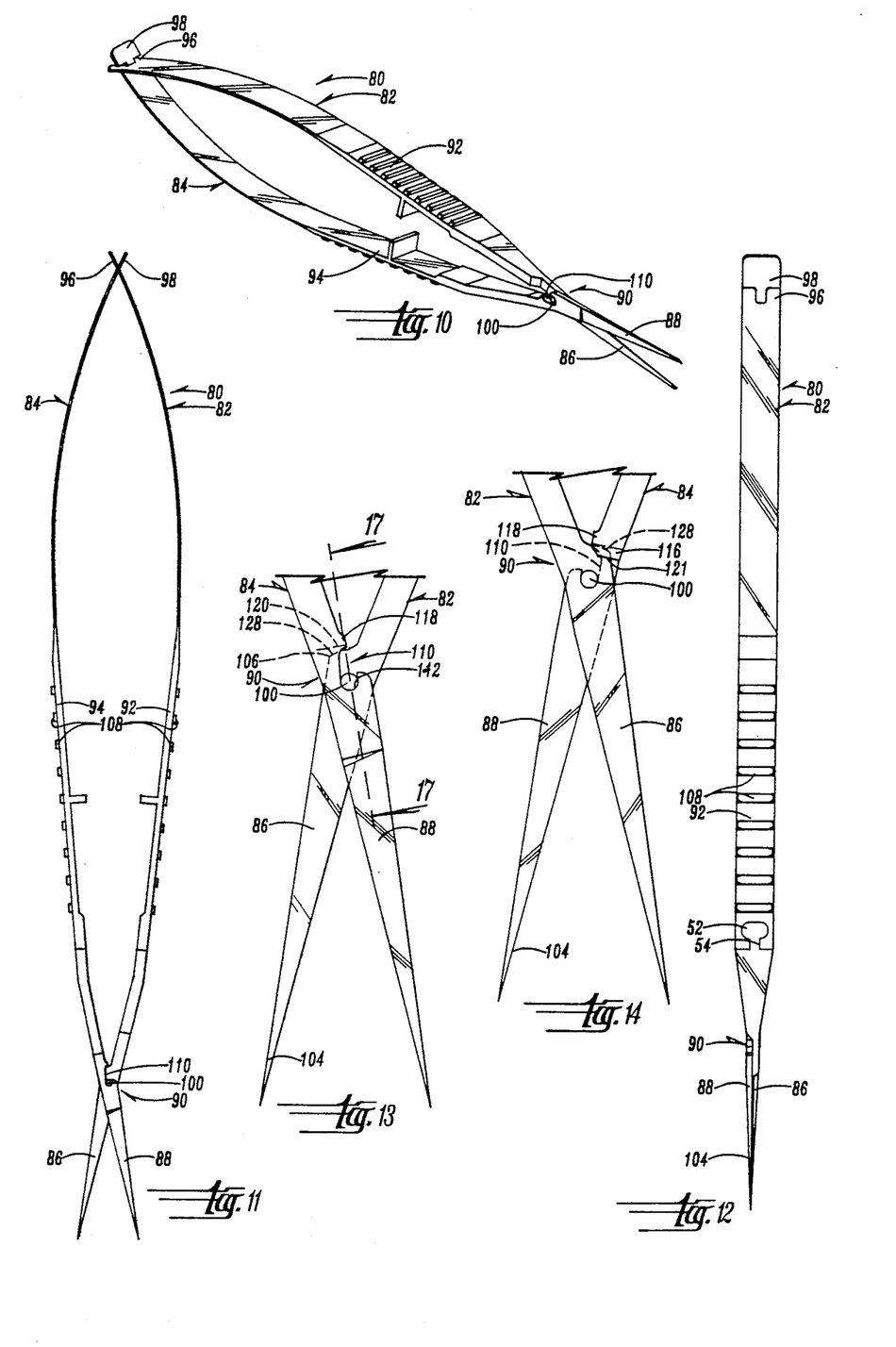
FIG. 10 is a perspective view of another embodiment according to the present invention.
FIG. 11 is an enlarged side view of the embodiment of FIG. 10.
FIG. 12 is a top plan view of FIG. 10.
FIG. 13 is a still further enlarged partial view of the pivot and blades of FIG. 11.
FIG. 14 is a reverse or back-side view of what is shown in FIG. 13, showing the blades in assembled position and in the range of operative cutting positions.

FIG. 10 shows embodiment 80 of detachable scissors. First and second handles 82 and 84 consist of blades 86 and 88, a pivot section 90, handles 92 and 94 on the opposite side of pivot section 90 from blades 86 and 88, and back ends 96 and 98, respectively.

Like the embodiment of FIGS. 1-9, pivot section 90 allows releasable assembly of arms 82 and 84, whereas the same releasable connection means as is shown in FIGS. 1-9 is utilized at back ends 96 and 98 of arms 82 and 84.

As can be seen in the enlarged views of FIGS. 11-14, pivot section 90 utilizes a pivot pin 100 which is separate from, but rigidly mounted within arm 82 in a transverse and perpendicular direction from the longitudinal axis of arm 82. It is to be understood that in this embodiment 80, pin 100 is press fitted within an aperture 102 (see FIG. 17) which rigidly holds it in place. By utilizing this construction, each profile of arms 82 and 84 can be cut with one pass of an EDM machine. The only substantial secondary machining that is required to be done to embodiment 80 is the relatively easy step of drilling aperture 102. Then the procedure of press fitting pin 100 therein is performed. It is further to be understood and appreciated that pin 100 is of such a length that it does not completely extend past the outer side surface of arm 82, but is installed and finished to present a virtually unitary surface on the outside of arm 82. No edges, extended portions, or crevices exist which would be detrimental to passing the blades and the following portions of the scissors into and through sensitive areas, or to cleaning and maintaining the scissors free from contaminating debris.

FIGS. 11-14 also show the structure of the arm 82 surrounding the location of pivot pin 100. Blade 86 begins from its pointed outer end 104 and is tapered to gradually widen to a point a short distance past the location of pivot pin 100. At that point (identified by reference numeral 106) arm 82 narrows to a somewhat constant width until generally the beginning of protrusions 108 on the exterior of handles 92 and 94, and narrows again between the end of protrusions 108 and back ends 96 and 98. The complete absence of any type of separately formed and outwardly extending flange or cam member such as in the embodiment of FIGS. 1-9 can clearly be seen.

On the other hand, in this embodiment arm 84 includes an aperture or opening 110 transversely through its cross section to mateably and pivotally receive pivot pin 100. Aperture 110 can have, in one form, a circular arcuate portion 112 which abuts pivot pin 100, when in assembled position such as shown in FIGS. 10-14, for approximately 180° around pivot pin 100. The remainder of pivot pin 100 is exposed, which in this embodiment, is in the rearward direction in relation to arm 84.

FIGS. 13 and 14 most clearly show that pivot pin 100 of handle 82 is retained in its position in circular arcuate portion 112 when arms 82 and 84 are assembled, and at least over the desired cutting range for blades 86 and 88 by virtue of a retaining means. The retaining means in this embodiment consists of the curved portion 128 of arm 82 immediately behind or rearward from point 106 (see FIG. 13), in combination with a slot 114 in arm 84 rearward and to the side of aperture or opening 110 (see in particular FIG. 18).

Slot 114 is an open sided channel defined between a narrow retaining wall 116 and a portion 118 (which defines the rearward portion of aperture or opening 110). Slot 114 is transverse through arm 84 and also is perpendicular to pivot pin 100.

As can be seen in FIG. 13, dashed line 120 indicates a plane defining the bottom of slot 114. The top or open end of slot 114 is defined by a plane parallel with plane 120 at and level with the top 121 of cantilever retaining wall 116 (see FIG. 14). By referring to FIGS. 13 and 14, when pivot pin 100 is within arcuate portion 112 so that scissors halves 82 and 84 are assembled, and blades 86 and 88 are spread apart into a maximum open cutting position, point 106 is within slot 114. Point 106 of arm 82 will be retained within slot 114 throughout any range of motion of blades 86 and 88 between the maximum open cutting position of FIG. 13, and a closed position for blades 86 and 88. This operation therefore insures that arms 82 and 84 will be held pivotally together such that pivot pin 100 forms an accurate, stable, and precise pivot point. It not only insures stability longitudinally between scissor arms 82 and 84, but also transversely in that the width of slot 114 is only slightly greater than the width of scissors arm 82 at and around point 106.

It can be appreciated that at least the portions of arms 82 and 84 depicted in FIGS. 13 and 14 are easily manufactured by cutting each profile in a single pass from a single piece of material. The sloped and smooth curves are easily manufactured and require essentially no machining after EDM cutting. Some final finishing and/or polishing may be required.

Likewise, slot 114 is easily manufactured without required secondary machining. Circular arcuate portion 112, and indeed the entire aperture 110, can also be cut and not further machined.

FIG. 12 shows the close structural cooperation of each of these elements involving both the pivot and the retaining portions for scissor arms 82 and 84. It is further noted that like the embodiment of FIGS. 1-9, a key 52 and slot 54 arrangement can be utilized to connect the portions of arms 82 and 84 having the retaining and pivot means, along with the blades, to the remainder of the handles.

Figure 15:
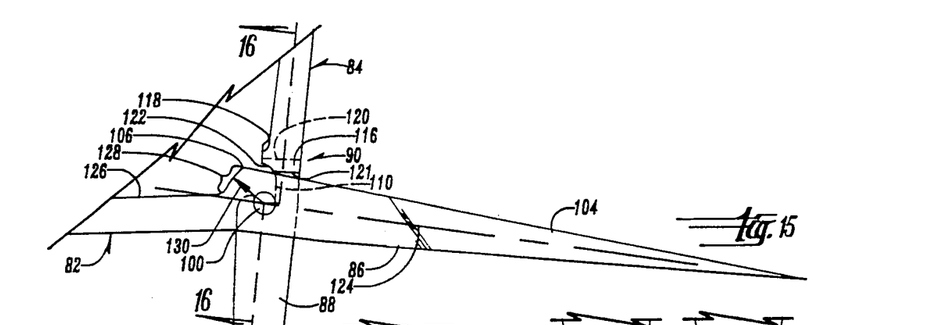
FIG. 15 is similar to FIG. 14 except showing the blades pivoting beyond the range of operative cutting positions to the point where the blades can be dissassembled.

As can be appreciated, when scissors arm 82 is pivoted from the position in FIGS. 13 and 14 to a position where point 106 of arm 82 moves out of slot 114 (see FIG. 16), arm 82 can be released and removed transversely and along the pivot axis of pivot pin 100 from arm 84. The orientation of arm 82 to arm 84 to accomplish this exists when arm 82 is generally perpendicularly pivoted with respect to arm 84, as shown in FIG. 15. Therefore, this feature allows the precise stable pivot joint needed for such scissors, without the risk that they will become separated during normal use, and even when moved somewhat beyond the normal cutting range. In the embodiment of FIGS. 1 through 9, the scissors halves can be separated at a point not much after the maximum open position of the blades is reached. In the embodiment of FIGS. 10-21, separation cannot occur until the arms are generally perpendicular, which removes this risk. Separation is still quick, easy, and allows complete cleaning. It requires removal of no parts and does not require use of tools. The structure of the embodiment of FIGS. 10-21 allows this advantageous feature while minimizing the procedure needed to separate the scissors halves, and therefore represents a preferred structure.

FIG. 15 shows how when arm 82 is pivoted to be generally perpendicular to arm 84, all portions of arm 82 are outside of slot 114. The only remaining abutment of arm 82 with arm 84 is pin 100 within circular arcuate portion 112 of aperture 110. Arms 82 and 84 can then easily be separated by moving them away from one another along the pivot axis through pivot pin 100.

FIG. 15 also shows how the angled front portion 122 of retaining wall 116 can be configured to allow retention of the scissors halves, yet allow very easy separation when in the position of FIG. 15. It does not present a sharp or fragile corner.

A center-line 124 through blade 86 of arm 82 is also shown to illustrate how it passes through the center of pivot pin 100 and then past curved surface 128. It can be seen in FIG. 15 how surface 126 of arm 82 then forms an outward expanding angle with line 124. It is noted also that surface 128 is an arc segment formed by a constant radius 130 to the center of pivot pin 100.

Figures 16, 17, 18:
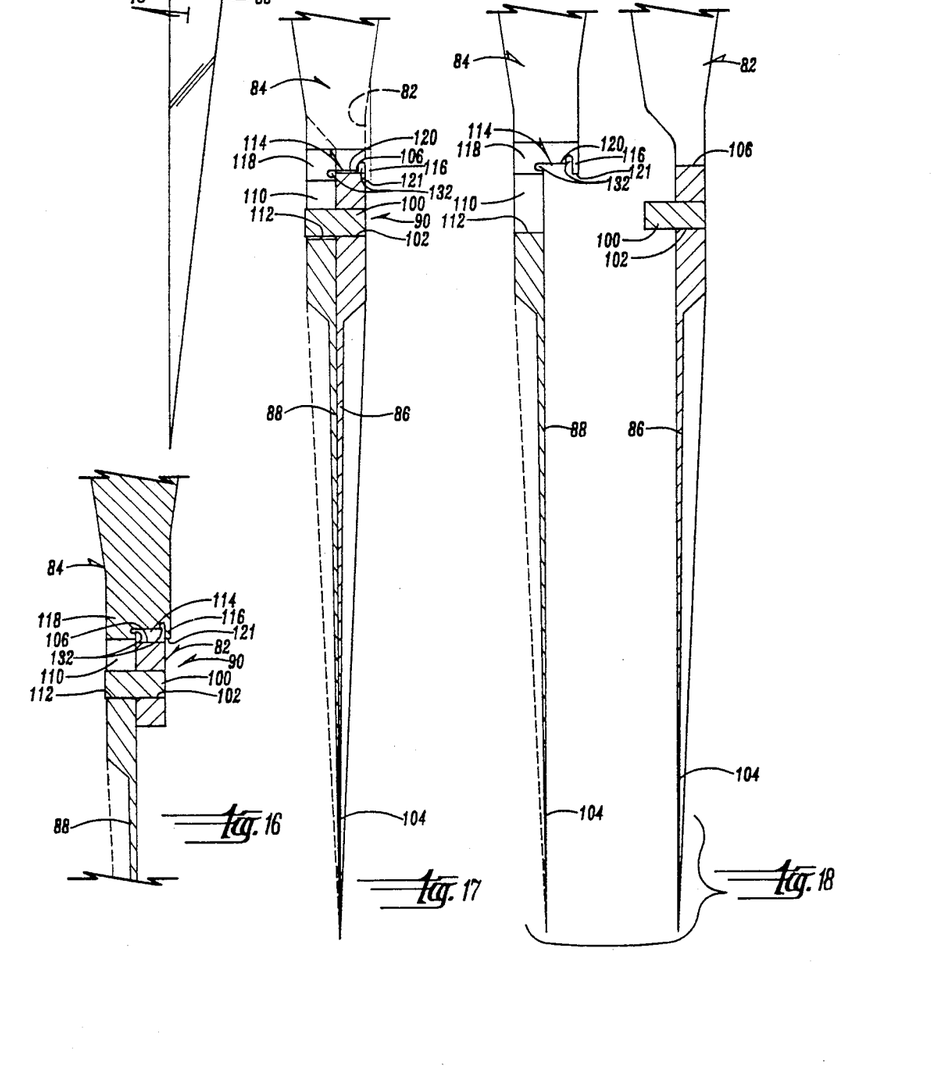
FIG. 16 is a sectional view taken along line 16—16 of FIG. 15.
FIG. 17 is a sectional view taken along line 17—17 of FIG. 13.
FIG. 18 is a view from the perspective of FIG. 17 but showing the blades and scissor halves disassembled.

FIG. 16 shows an enlarged cross section of this relationship. It also shows in detail how pivot pin 100 is press fitted into arm 82 as well as how arm 82 is completely out of slot 114 when in a generally perpendicular position to arm 84. It is to be understood that small kerfs 132 may be formed by the wire of an EDM machine cutting slot 114 without effecting the structure. This illustrates how efficiently the structure can be produced with a wire EDM machine.

FIG. 17 depicts scissor halves 82 and 84 in assembled and closed form, but with portions in cross section.

FIG. 18 shows those same parts of arms 82 and 84 disassembled and separated, but positioned parallel and side by side.

Figure 19:
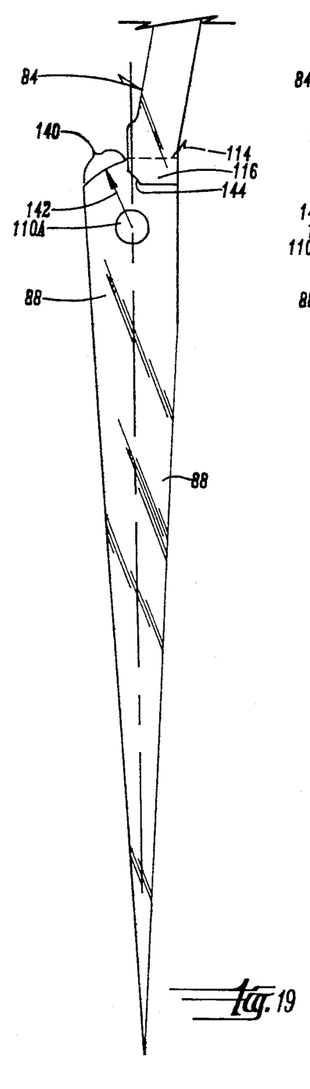
FIG. 19 is a partial side view of a scissors arm according to the invention showing an alternative embodiment of an aperture to slidably receive the pivot pin mounted in the other scissors arm.
Figure 20:
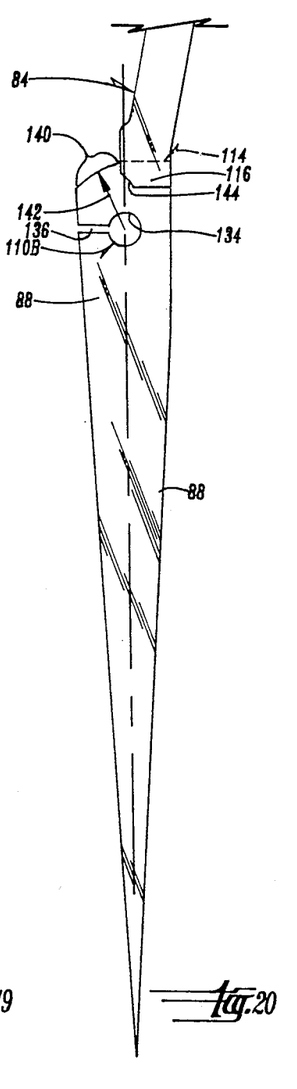
FIG. 20 is a partial side view like FIG. 19 showing a still further alternative embodiment of an aperture to slidably receive the pivot pin mounted in the other scissors arm or, optionally, be used to mount the pivot pin, if used in the opposite scissors arm.
Figure 21:
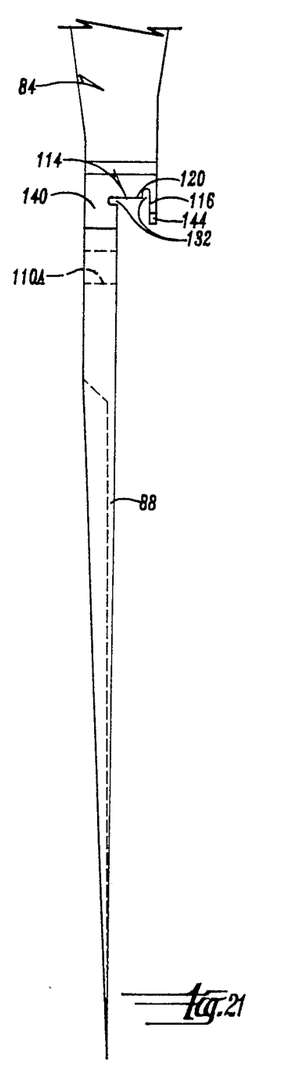
FIG. 21 is a top plan view of FIG. 19.

FIGS. 19-21 illustrate how the aperture receiving pivot pin 100 can alternatively take the form of simply a bored or drilled hole 110A (FIG. 19) or a keyhole shaped aperture 110B (FIG. 20) which includes a circular portion 134 receiving pin 100 and an open channel 136 to allow a traveling wire of an EDM machine to cut through arm 84 to form the circular portion.

Specifically referring to FIG. 19, it can be seen that circular hole 110A is utilized instead of the aperture or opening 110 in the embodiment in FIGS. 1-9 to palatably receive pivot pin mounted in and extending from the other scissors arm 82. Therefore, instead of having the opening 110, with the partial arcuate portion 112, only a simple hole 110A needs to be drilled into scissors arm 84.

In comparison, FIG. 20 is identical to FIG. 19, except that it shows an alternative aperture 110B in scissors arm 84. Aperture 110B includes a circular hole portion 134 which functions to receive a pivot pin 100 mounted in a scissors arm 82. The difference with aperture 110B is that a narrow channel 136 extends from an edge of arm 84 inwardly to the circular portion 134.

Both embodiments of FIGS. 19 and 20 are otherwise the same in other respects to arm 84 in FIGS. 10-18. A retaining means is still incorporated into arm 84, consisting of a slot 114 and a retaining wall 116. These parts cooperate to receive convex edge 128 of an arm 82 the same as that shown in the embodiment of FIGS. 10-18. Thus, the rather complex shape of aperture 110 of the embodiment of FIGS. 10-18 is avoided and substituted by the simplicity of hole 110A, which would require a relatively simple secondary machining forming that hole, or the aperture 110B which can be cut on the first pass of cutting arm 84 by traveling wire EDM machine.

It is to be understood that both embodiments of arm 84 shown in FIGS. 19 and 20 include a curved edge 140 defined by a radius 142 from the center of aperture 110A or 110B, which is similar to curved edge 128 of arm 82 in FIGS. 10-18. Also, it is pointed out that wall 116 includes a beveled portion 144 similar to portion 122 previously described with regard to FIGS. 10-18.

Finally, it is to be understood that scissors 80 could be constructed so that arm 84 utilizes aperture 110 as shown in FIGS. 10-18, aperture 110A of FIG. 19, or aperture 110B of FIG. 20. Moreover, it is to be understood that arm 82 could utilize either the drilled hole 102 shown in FIG. 18, or an aperture like 110B (shown in FIG. 20) into which can be mounted pivot pin 100. The structure of aperture 110B allows some flexing of the material around the circular portion 134 to allow press fitting of a pin 100. It is also advantageous in that it allows some margin of error for tolerances of diameter of the pivot pin 100.

This interchangeability of apertures in either arms 82 or 84, all functioning according to the present invention, would also allow pivot pin to be mounted in either arm 82 or 84. For example, if arm 84 utilized aperture 110B, and its corresponding opposite arm 82 utilized aperture 110B, the diameter of the circular portion of aperture 110B can be cut so that a pivot pin 100 could be press fit into one of the apertures 110B and either arm 82 or 84, with the corresponding aperture 110B being cut of a diameter to be slightly larger than pin 100 to allow it to slidably and pivotably be inserted therein. By further example, both arms 82 and 84 can utilize a simple drilled hole 110A, with one of the holes being of a diameter to allow pin 100 to be press fitted and retained therein, and the other hole being of slightly larger diameter than the outside diameter of pin 100.

FIG. 21 shows a top view of arm 84 of FIG. 19, and clearly shows how aperture 110A can be substituted for aperture 110 of FIGS. 10-18.

What is claimed is:

1. A surgical scissors having first and second scissors halves pivotally connected at a pivot axis between blades and handles of the scissors, the improvement comprising:
   releasable pivot joint means for allowing disassembly of the first and second scissors halves;
   the pivot joint means including a pin defining the pivot axis extending from one of said first and second scissors halves;
   an aperture in the other of said first and second scissors halves for slidably receiving and pivotally retaining said pin;
   a channel in one of the first and second scissors halves, the channel being generally perpendicular to and presenting an open face in the direction of the pivot axis, and a retaining wall forming one side of the channel, a retaining portion formed in the other of the first and second scissors halves, the retaining portion being generally perpendicular to and presenting a surface which is at least partially retained in the channel through a range of cutting motions defined by a maximum open position of the blades and a closed position of the blades; and
   the retaining portion being completely outside the channel upon movement of the first and second scissors halves to a position where the blades are pass the maximum open position and are generally perpendicular to one another, which allows separation of the first and second scissors halves along the pivot axis by withdrawal of the pin from the aperture.

2. A disassemblable scissors means comprising:
   a pair of opposing, pivoted arms having scissors blades and opposed handles on opposite sides of a pivot point;
   a pivot means associated with the arms forming the pivot point, the pivot means allowing releasable assembly of the arms, the pivot means comprising a pin and aperture, each in opposite arms, forming the pivot point, the pin extending from one arm towards the other for insertion into the aperture in the other arm which extends transversely and at least partially through the other arm, the aperture comprising an opening having at least a portion open and a portion which is closed and arcuate; and
   a retaining means associated with the arms for disallowing separation of the arms when assembled unless the arms are pivoted with respect to one another to at least an approximate perpendicular orientation.

3. A disassemblable scissors means comprising:
   a pair of opposing, pivoted arms having scissors blades and opposed handles on opposite sides of a pivot point;
   a pivot means associated with the arms forming the pivot point, the pivot means allowing releasable assembly of the arms, the pivot means comprising a pin and aperture, each in opposite arms, forming the pivot point, the pin extending from one arm towards the other for insertion into the aperture in the other arm which extends transversely and at least partially through the other arm, the aperture comprising a circular bore through one of said arms; and
   a retaining means associated with the arms for disallowing separation of the arms when assembled unless the arms are pivoted with respect to one another to at least an approximate perpendicular orientation.

4. The means of claim 3 further comprising a channel from an edge of the arm to the bore.

5. A disassemblable scissors means comprising:
   a pair of opposing, pivoted arms having scissors blades and opposed handles on opposite sides of a pivot point;
   a pivot means associated with the arms forming the pivot point, the pivot means allowing releasable assembly of the arms;
   a retaining means associated with the arms for disallowing separation of the arms when assembled unless the arms are pivoted with respect to one another to at least an approximate perpendicular orientation;
   said retaining means comprising a male member which is a portion of one arm, and a female member which is a portion of the other arm; and
   said male member comprising a uniform thickness and a width which is at least equal to other portions of said one arm, and said female member is a slot through which said male member is movably retained.

* * * * *